(12) United States Patent
Chiu et al.

(10) Patent No.: US 9,272,960 B2
(45) Date of Patent: Mar. 1, 2016

(54) **METHODS FOR PREPARATION OF LYCOPENES FROM C15-WITTIG SALTS AND METHODS FOR PURIFICATION OF HIGH ALL-*E* CONTAINING AND HIGH 6Z CONTAINING C15-WITTIG SALTS**

(71) Applicant: Allied Biotech Corp., Taipei (TW)

(72) Inventors: Haw-Shyi Chiu, Taoyuan (TW); Po-Wei Lin, Taoyuan (TW)

(73) Assignee: Allied Biotech Corp. (TW)

( * ) Notice: Subject to any disclaimer, the term of this patent is extended or adjusted under 35 U.S.C. 154(b) by 0 days.

(21) Appl. No.: 14/327,058

(22) Filed: Jul. 9, 2014

(65) Prior Publication Data

US 2016/0009611 A1  Jan. 14, 2016

(51) Int. Cl.
*C07C 1/34* (2006.01)
*C07F 9/54* (2006.01)
*C07C 11/21* (2006.01)

(52) U.S. Cl.
CPC . *C07C 1/34* (2013.01); *C07C 11/21* (2013.01); *C07F 9/5442* (2013.01)

(58) Field of Classification Search
CPC .......... C07C 1/34; C07C 11/21; C07F 9/5442
See application file for complete search history.

(56) References Cited

U.S. PATENT DOCUMENTS 7,126,036 B2 * 10/2006 Wegner et al. ................ 585/351
2002/0128516 A1 * 9/2002 Wegner et al. .................... 568/8

OTHER PUBLICATIONS

Takehara et al (Journal of Agricultural and food chemistry, 2014, 62, 264-269).*

* cited by examiner

*Primary Examiner* — Sudhakar Katakam
(74) *Attorney, Agent, or Firm* — Bacon & Thomas, PLLC

(57) ABSTRACT

The present invention relates to methods for preparation of lycopenes, especially to lycopenes with high all-E contents or high 6Z contents from C15-Wittig slats mixtures. (with high all-E-contents and high 6Z-contents, respectively). C15-Wittig slats mixtures are purified and 6Z-C15-Wittig salts are extracted from the mixtures. The extracted 6Z-C15-Wittig salts are, used in the synthesis of lycopenes with high 6Z contents and the residues are used in the synthesis of lycopenes with high All-E contents.

16 Claims, No Drawings

METHODS FOR PREPARATION OF LYCOPENES FROM C15-WITTIG SALTS AND METHODS FOR PURIFICATION OF HIGH ALL-E CONTAINING AND HIGH 6Z CONTAINING C15-WITTIG SALTS

FIELD OF THE INVENTION

The present invention relates to methods for preparation of lycopenes, especially to lycopenes with high all-E contents or high 6Z contents from C15-Wittig slats mixtures. In this invention, methods for extraction and purification of desired E/Z ratios in C15-Wittig salts are also disclosed.

BACKGROUND OF THE INVENTION

Lycopene (also referred to as Ψ,Ψ-carotene) is one of the many carotenoids that exist in nature. Lycopene can be easily found in ripe tomato fruits, watermelons and pink grapefruits, giving them a characteristic red pigmentation. Lycopene obtained from raw tomatoes contains approximately 5% or more of cis-lycopene. According Schierle et al. 1997, lycopene obtained from raw tomatoes contains 94-96% of all-E-lycopene, 3-5% of 5Z-lycopene and a minor quantity of Z-isomers. Recent epidemiological studies show that lycopene as antioxidant may alleviate coronary heart disease and cancers of prostate, bladder, skin, digestive tract, breast and cervix.

Lycopene can be produced in two ways: extraction and synthesis. Biological lycopene is extracted either from fruits (such as tomatoes or watermelons) or from fungal biomass (such as *Blakeslea trispora*). Synthetic lycopene is manufactured through chemical synthesis. Lycopene produced by using synthesis process has lower all-E content than that extracted from *B. trispora*. The joint FAO (Food and Agriculture Organization of the United Nations)/WHO (World Health Organization) expert committee has established specifications for both synthetic lycopene and lycopene extracted from *B. trispora* at the 67th meeting of JECFA (2006). For synthetic lycopene, total lycopene content shall be higher than 96%, in which at least 70% must be all-E-lycopene and the remains are 5Z-lycopene and a minor quantity of Z-isomers. For lycopene extracted from *B. trispora*, the total lycopene content shall be higher than 95%, in which at least 90% must be all-E-lycopene and the remains are other carotenoids (β- and γ-carotene) for not more than 5%. These specifications indicate that lycopene extracted from *B. trispora* consists mainly of all-E-form, which no synthetic lycopene prepared using the nowadays technology may reach.

Pseudoionone is one of the starting materials for lycopene syntheses. It is a mixture of cis and trans isomers (also referred to as the cis/trans mixture). In general, pseudoionone cis/trans mixtures containing about 20% to 50% of all-trans-isomer and the remains of other cis-isomers are available in the market. A cis-pseudoionone will result in a cis-lycopene and an all-trans-pseudoionone will result in an all-E-lycopene, after the syntheses. In order to obtain higher all-E containing lycopene, a pseudoionone with higher all-trans content shall be used. Therefore, the all-trans-pseudoionone must first be separated from the pseudoionone cis/trans mixture before the syntheses. In the conventional technology, all-trans-pseudoionone is isolated from the cis/trans mixture by a fractional distillation operation. This purified all-trans-pseudoionone so obtained is then used to synthesize a C15 phosphonium salt to produce lycopene.

Unfortunately, the conventional synthesis process in producing the C15 phosphonium salts will cause a part of the all-trans-form to convert to cis-forms during the reaction. With the current technology, even the high all-E containing (90% to 95%) C15-OH (also referred to as 3,7,11-trimethyl-dodeca-1,4,6,10-tetraen-3-ol or vinyl-pseudoionol) is used, a product with only 65.2% to 71.1% of all-E-C15-Wittig salts, as well as 9.8% to 10.3% of 6Z and 8.2% to 10.8% of 2Z isomers, would be obtained. Clearly, the resulted products have lower E isomer/Z isomer ratios, which are about 3.4:1 to 3.8:1. Reference may be made to, for example, U.S. Pat. No. 6,603,045, U.S. Pat. No. 6,433,226, U.S. Pat. No. 6,187,959 and U.S. Pat. No. 2002/0,128,516. Such poor E/Z selectivity of C15 phosphonium salts is a challenge in producing a synthetic all-E-lycopene, with all-E content competitive to that of biological lycopenes extracted from natural sources such as *B. trispora*.

The other method for producing synthetic all-E-lycopenes uses thermal isomerization process that converts Z-isomers of lycopene into all-E-lycopene. Reference may be made to U.S. Pat. No. 7,126,036 and U.S. Pat. No. 2004/0049082. This process increases the all-E content of the obtained lycopene from 53% to 73.4%-87.8%.

It has been found that all-E-C15-Wittig salts can be separated from the C15 phosphonium salt obtained from the reaction of cis/trans mixture, using a series of purification steps in aprotic solvents. According to the present invention, significantly high E/Z selectivity in the C15 phosphonium salts, with an E isomer/Z isomer ratio of greater than 15:1, may be realized. By reacting a C10-dialdehyde (also referred to as 2,7-dimethyl-2,4,6-octatriene-1,8-dial) with such high all-E content of C15-Wittig salts through a double Wittig reaction, a synthetic lycopene with all-E content for up to 95% may be produced. The obtained all-E content may even satisfy the all-E content specification for biological lycopenes. By switching the reactants from high all-E content of C15-Wittig salts to high 6Z content of C15 phosphonium salts, a synthetic lycopene with a 5Z-content of up to 97% is also obtained.

SUMMARY OF THE INVENTION

According to the present invention, new methods for the preparation of all-E-lycopenes and 5Z-lycopenes are disclosed. The methods generally include the steps of purification of all-E-C15-Wittig salts and synthesis of all-E-Lycopene and 5Z-Lycopene using the purified all-E-C15-Wittig salts. According to this invention, by changing the combination of solvents used and the reaction temperature, C15-Witting salts of a variety of E isomer/Z isomer ratio may be obtained. The invented methods may further comprise synthesis of C15-OH, to be used as material for the all-E-C15-Wittig salts.

In the purification of all-E-C15-Wittig salts, a C15 Wittig salt cis/trans mixture, preferably a C15 phosphonium salt cis/trans mixture, containing about 40% of all-E content is first obtained. The C15 Wittig salt cis/trans mixture is preferably a product of synthesis of all-E-C15-Witting salts, whereby it contains both cis and trans forms of isomers. The C15 Wittig salt cis/trans mixture is concentrated under vacuum to remove methanol and $H_2O$ contained therein, whereby a C15-Wittig salt precipitate is obtained. An aprotic solvent is added to the precipitate for further concentration. The aprotic solvent may be ethyl acetate, chloroform, acetone, methyl ethyl ketone or methyl isobutyl ketone, or any combination thereof, and is preferably ethyl acetate. The concentration takes place at around 30° C. for a relatively long period of time, such as 16 hours. A crystallized C15-Wittig salt precipitate is obtained. An aprotic solvent is later added to the precipitate for extraction of 6Z-C15-Wittig salts.

The aprotic solvent may be ethyl acetate, chloroform, acetone, methyl ethyl ketone or methyl isobutyl ketone, or any combination thereof, and is preferably acetone. The extraction operation takes place at between 0° C. to 55° C., preferably 40° C. to 50° C., for about 2 hours. After filtration, a wet cake of 6Z-C15-Wittig salt is obtained. The 6Z-C15-Wittig salt wet cake is removed and the filtrate is concentrated again, to obtain C15-Wittig salts with an E isomer/Z isomer ratio of greater than 3:1.

In order to obtain C15-Wittig salts with high all-E contents, an aprotic solvent in either a pure solvent form or a solvent mixture form is added to the C15-Wittig salts, i.e, the filtrate after the wet cake of 6Z-C15-Wittig salt is removed after the filtration step, for crystallization. The aprotic solvent may be ethyl acetate, chloroform, acetone, methyl ethyl ketone or methyl isobutyl ketone, or any combination thereof, and is preferably an ethyl acetate/acetone mixture. The crystallization operation takes place at between 25° C. to –30° C. for a relatively long time, preferably 0° C. to –20° C. for about 16 hours. After filtration and drying, C15-Wittig salts with an E isomer/Z isomer ratio of greater than 15:1 are obtained.

In order to obtain C15-Wittig salts with high 6Z contents, the wet cake of 6Z-C15-Wittig salts obtained in the previous filtration step is rinsed in an aprotic solvent. The aprotic solvent may be acetone, methyl ethyl ketone or methyl isobutyl ketone, or any combination thereof, and is preferably acetone. The rinsing operation takes place at between 0° C. to 55° C., preferably 40° C. to 50° C., for about 2 hours. After filtration and drying, C15-Wittig salts with an E isomer/Z isomer ratio of less than 1:30 are obtained.

In the synthesis of lycopenes, i.e., all-E-lycopene and 5Z-lycopene, products obtained from the purification step are reacted with C10-dialdehyde in a double Wittig reaction. A base reactant may be added to proceed the reaction. After thermal isomerization and filtration, a lycopene wet cake is collected. The product is washed, rinsed, filtered and dried to obtain all-E-lycopene powders with an all-E content of up to 95%, or 5Z-lycopene powders with a 5Z content of up to 97%.

In the optional synthesis step of C15-OH, the C15 phosphonium salt cis/trans mixtures may be prepared by reacting vinyl-pseudoionol and triphenylphosphine with an inorganic or organic acid, preferably a strong inorganic or organic acid. The strong acid may be a hydrohalic acid such as hydrochloric acid and hydrobromic acid, sulfuric acid, phosphoric acid, sulfonic acid and other inorganic or any organic acid with a comparable degree of dissociation.

DETAILED DESCRIPTION OF THE INVENTION

The present invention discloses novel methods for the preparation of all-E-lycopenes and 5Z-lycopenes. The invented methods feature in their capability of producing C15-Wittig salts with controllable E isomer/Z isomer ratios and synthesis of all-E-lycopenes and 5Z-lycopenes using the particular C15-Wittig salts. All-E-lycopenes with an all-E content of up to 95% or 5Z-lycopenes with a 5Z content of up to 97% are obtained by using the method of this invention.

The invented methods generally include the steps of purification of C15-Wittig salts and synthesis of all-E-lycopenes and 5Z-lycopenes using the purified C15-Wittig salts. In the purification of C15-Wittig salts, a C15 phosphonium salt cis/trans mixture is first obtained. The mixture is preferably a product from the synthesis of C15-Wittig salts, using the conventional synthesis methods. The mixture is first concentrated under vacuum to remove as much methanol/$H_2O$ as possible, if it is produced in a previous synthesis step. After enough quantity of methanol/$H_2O$ is removed, a C15-Wittig salt precipitate is emerged. The concentration takes place at around 30° C. for a relatively long period of time, such as 16 hours.

According to this invention, by changing the combination of aprotic solvents used and the reaction temperature, C15-Wittig salts of desired E isomer/Z isomer ratio may be obtained. For example, among the Wittig salts, both all-E-C15-Wittig salts and 6Z-C15-Wittig salts have poorer solubility than 2Z-C15-Wittig salts in ethyl acetate. On the other hand, both 2Z-C15-Wittig salts and all-E-C15-Wittig salts have much better solubility than 6Z-C15-Wittig salts in either acetone, methyl ethyl ketone or methyl isobutyl ketone. The solubility of 6Z-C15-Wittig salts in acetone, methyl ethyl ketone or methyl isobutyl ketone also varies with temperature. It is therefore possible to control the E isomer/Z isomer ratios in the resulted C15-Wittig salts by changing the combination of the aprotic solvents as well as the purification temperature.

An aprotic solvent is later added to the precipitate for extraction of 6Z-C15-Wittig salts. The aprotic solvent may be ethyl acetate, chloroform, acetone, methyl ethyl ketone or methyl isobutyl ketone, or any combination thereof, and is preferably acetone. The extraction operation takes place at between 0° C. to 55° C., preferably 40° C. to 50° C., for about 2 hours. After filtration, a wet cake of 6Z-C15-Wittig salt is obtained. The 6Z-C15-Wittig salt wet cake is removed. The filtrate is again concentrated in an aprotic solvent, preferably ethyl acetate, to obtain C15-Wittig salts having an E isomer/Z isomer ratio of greater than 3:1. The E isomer content in the product is relatively low but the product is useful in direct reaction with a C10-dialdehyde without further purification, to produce a qualified (high all-E content) synthetic lycopene.

In order to obtain higher all-E content of C15-Wittig salts, an aprotic solvent in either a pure solvent form or a solvent mixture form is added to the C15-Wittig salts obtained in the previous extraction step for crystallization. The aprotic solvent is preferably ethyl acetate. The crystallization operation may take place under the temperature of between 25° C. to –30° C. for a predetermined period of time, preferably under 0° C. to –20° C. for, for example, 16 hours. The produced wet cake may be further purified in an ethyl acetate/acetone solvent. The products are filtered and dried to obtain high all-E content of C15-Wittig salts with an E isomer/Z isomer ratio of greater than 15:1.

In order to obtain C15-Wittig salts with high 6Z content, the wet cake of 6Z-C15-Wittig salts obtained in the above-mentioned extraction step is subjected to further purification. An aprotic solvent is added to the wet cake. Aprotic solvents applicable in this purification step include acetone, methyl ethyl ketone and methyl isobutyl ketone and any of their combinations. The purification is operated under the temperature of 0° C. to 55° C., preferably 40° C. to 50° C., for a period of time such as 2 hours. The products are filtered and dried to obtain a high 6Z content of C15-Wittig salts with an E isomer/Z isomer ratio of less than 1:30.

In the synthesis of lycopene, C10-dialdehyde is reacting with products of the purification steps. The high all-E content or high 6Z content of C15-Wittig salts obtained in the purification process is reacted with the C10-dialdehyde in a double Wittig reaction. A base reactant may be added to proceed the reaction. The product is then processed by thermal isomerization and filtration, to obtain a lycopene wet cake. Acetone and water are added separately for washing and rinsing treatments. After filtration and drying, all-E-lycopene powders with all-E content of up to 95% or 5Z-lycopene powders with 5Z content of up to 97% are obtained.

The invented methods may include optionally synthesis of C15-OH, to be used as the C15-Wittig salts. In the synthesis of C15-OH, a purified pseudoionone (Fluka, E/Z=2.7:1) is reacted with vinyl magnesium chloride. Since the reactant, pseudoionone, is a cis/trans mixture, the produced C15-OH is also a cis/trans mixture and has the same level of E isomer/Z isomer ratio as in the pseudoionone. Thereafter, the C15-OH is reacted with a triphenylphosphine and a strong acid, to produce the desired C15 phosphonium salts. The resulted C15 phosphonium salt is also a cis/trans mixture, containing about 40% of all-E content.

According to the present invention, methods that produce C15-Wittig salts with almost any desirable E isomer/Z isomer ratio are provided. As a result, lycopenes with almost any desirable E isomer/Z isomer ratio of lycopene may also be prepared, using the C15-Wittig salts, purified according to this invention, as material. The present invention provides new methods of producing desirable synthetic lycopene.

In the followings, embodiments in the purification of C15-Wittig salts and in the synthesis of all-E-lycopenes and 5Z-lycopenes using the purified C15-Wittig salts will be illustrated.

Preparation of C15-TPP Salts with High all-E Content or High 6Z Content

Example 1

250.0 g of 3,7,11-trimethyldodeca-2,4,6,10-tetraen-1-yl-triphenylphosphonium chloride salt solution (purity 38.6% in methanol) with 40.9% of all-E content, 38.7%, of, 6Z content and 4.1% of 2Z content (E isomer/Z isomer ratio=1:1) were concentrated by vacuum distillation at 30° C., to remove methanol solvent. Then 135 g of ethyl acetate were added. After concentration by vacuum distillation, 60 g of ethyl acetate was added in addition. The salt solution was then heated to 30° C. and stirred for 16 hours. Thereafter, 120 g of acetone was added into the mixture. Temperature was raised to 50° C. and maintained for 2 hours then lowered to 30° C. The products were filtered to obtained solid phase 3,7,11-trimethyldodeca-2E,4E,6Z,10E-tetraen-1-yl-triphenylphosphonium chloride (6Z-C15TPPC1) salt wet cake in the amount of 48.5 g (assay 6z-%=73.3%; assay All E %=12%). The wet cake was removed and the filtrate was concentrated at 50° C. by vacuum distillation. Thereafter, the concentrated filtrate was added 197 g of ethyl acetate, cooled to −20° C. and stirred for 16 hours. A 3,7,11-trimethyldodeca-2E,4E,6E,10E-tetraen-1-yl-triphenylphosphonium chloride salt wet cake was obtained by filtration. 167 ml of ethyl acetate and 33 ml of acetone were added to the obtained wet cake. The mixture was stirred at 25° C. for 30 minutes then cooled to 5° C. and stirred for 16 hours. After filtration and drying, 30 g of 3,7,11-trimethyl-dodeca-2E,4E,6E,10E-tetraen-1-yl-triphenyl phosphonium chloride (All E-C15TPPC1) salt powder were obtained. HPLC analysis revealed that the powder contains 94.8% of all-E isomer, 3.3% of 6Z isomer, and 1.9% of 2Z isomer. The E isomer/Z isomer ratio is accordingly 18.2:1.

Example 2

1,534.0 g of a 3,7,11-trimethyldodeca-2,4,6,10-tetraen-1-yl-triphenylphosphonium chloride salt solution (purity 38.6% in methanol) with 42.6% of all-E isomer, 39.6% of 6Z and 2Z isomers (E isomer/Z isomer ratio=1.1:1) were concentrated by vacuum distillation at 30° C., followed by adding 400 ml of ethyl acetate and stirring for 16 hours. 400 ml of acetone were added and the mixture was stirred for additional 2 hours. After filtration, the obtained 230 g of solid phase 3,7,11-trimethyldodeca-2E,4E,6Z,10E-tetraen-1-yl-triphenylphosphonium chloride salt wet cake were removed and an filtrate was obtained. The filtrate was then concentrated by vacuum distillation at 45° C., to remove the solvent, whereby 640 g of residue (purity of C15 salts: 55.2%) were obtained. HPLC analysis revealed that the residue contains 77.2% of all-E isomer, 13.8% of 6Z isomer and 9.0% of 2Z isomer. Its E isomer/Z isomer ratio is accordingly 3.4:1.

Example 3

500.0 g of 3,7,11-trimethyldodeca-2E,4E,6Z,10E-tetraen-1-yl-triphenylphosphonium chloride salt wet cake obtained from example 1, with 12.0% of all-E isomer, 73.3% of 6Z isomer and 0.3% of 2Z isomer (E isomer/Z isomer ratio=1:6.1) was suspended in 1,000 ml of acetone. The salt solution was then heated to 40° C. and stirred for 1 hour. After filtration and drying, 362.0 g of 3,7,11-trimethyldodeca-2E,4E,6Z,10E-tetraen-1-yl-triphenyl phosphonium chloride salt powder were obtained. HPLC analysis revealed that the powder obtained C15 phosphonium salt powder contained 2.9% of all-E isomer, 96.8% of 6Z isomer and 0.3% of 2Z isomer. The E isomer/Z isomer ratio is accordingly 1:33.5.

Synthesis of all-E-Lycopene or 5Z-Lycopene

Example 4

89.0 g of 3,7,11-trimethyldodeca-2E,4E,6E,10E-tetraen-1-yl-triphenylphosphonium chloride salt powder (purity 95.2%, E isomer/Z isomer ratio=15.8:1) and 9.3 g of 2,7-dimethyl-2,4,6-octatriene-1,8-dial were added into 90 g of methanol. The temperature of the composition was raised to 30° C. and maintained for 30 minutes. After 95 g of an ethyl acetate/n-heptane (w/w=1:1) solvent mixture were added, the solution mixture was cooled to room temperature. Then 175.5 g of a potassium carbonate solution by dissolving 63.5 g of potassium carbonate powder in 112 g of water were added dropwise. The solution mixture was then heated to 60° C. and maintained for 3 hours. Thereafter, the temperature of the solution mixture was raised to 100° C. to remove as much organic solvents as possible, then cooled to 80° C. and maintained for 16 hours. After filtration, 94.3 g of high all-E-lycopene wet cake were obtained. Acetone and water were added to the wet cake separately for washing and rinsing treatments. After filtration and drying, 24.5 g of high all-E-lycopene crystal were obtained. HPLC analysis revealed the lycopene crystal contained 95.3% of all-E-lycopene, and 3.3% of 5Z-lycopene. UV assay of the lycopene=101.0%.

Example 5

50.0 g of 3,7,11-trimethyldodeca-2E,4E,6Z,10E-tetraen-1-yl-triphenylphosphonium chloride salt powder (purity 89.8%, E isomer/Z isomer ratio=1:33.1) and 5.4 g of 2,7-dimethyl-2,4,6-octatriene-1,8-dial were added into 60 ml of methanol. The temperature of the composition was raised to 30° C. and maintained for 30 minutes. After 55 g of an ethyl acetate/n-heptane (w/w=1:1) solvent mixture were added, the solution mixture was cooled to room temperature. Then 103.5 g of a potassium carbonate solution by dissolving 37.5 g of potassium carbonate powder in 66 g of water were added dropwise. The solution mixture was heated to 60° C. and maintained for 3 hours. Thereafter, the temperature of the solution mixture was raised to 100° C. to remove as much organic solvents as possible, then cooled to 80° C. and maintained for 16 hours. After filtration 62.0 g of 5Z-lycopene wet cake were obtained. Acetone and water were added to the wet cake separately for washing and rinsing treatments. After filtration and drying, 16.1 g of high 5Z-lycopene containing crystal were obtained. HPLC analysis revealed the lycopene crystal contained 97.9% of 5Z-lycopene and 1.4% of other Z-isomers. UV assay of the lycopene=100.5%.

Example 6

203.0 g of 3,7,11-trimethyldodeca-2,4,6,10-tetraen-1-yl-triphenylphosphonium chloride salt solution (purity 58.4%, E isomer/Z isomer ratio=3.4:1) and 14.4 g of 2,7-dimethyl-2,4,6-octatriene-1,8-dial were added into 55 ml of methanol. After 316 ml of an ethyl acetate/n-heptane (w/w=1:1) solvent mixture were added, the solution mixture was heated to 30° C. Then 470.0 g of a potassium carbonate solution by dissolving 170.0 g of potassium carbonate powder in 300 g of water were added dropwise. The solution mixture was heated to 60° C. and stirred for 3 hours. Thereafter, the temperature of the solution mixture was raised to 100° C. to remove as much organic solvents as possible, then cooled to 80° C. and stirred for 16 hours. 95.9 g of lycopene wet cake were obtained by filtration. Acetone and water were added to the wet cake separately for washing and rinsing treatments. After filtration and drying, 24.6 g of synthetic lycopene crystal were obtained. HPLC analysis revealed the lycopene crystal contained 75.7% of all-E-lycopene, 19.2% of 5Z-lycopene and 3.1% of other Z-isomers. UV assay of the lycopene=99.0%.

EFFECTS OF THE INVENTION

Lycopene is one of the many carotenoids that may alleviate coronary heart disease and prevent from several kinds of cancers. It can be produced by way of either extraction or synthesis. Current synthesis processes can produce synthetic lycopenes with all-E content of merely 87%, which is much lower than that of the biological lycopene extracted from *B. trispora*/natural source. This invention makes the synthetic lycopene to meet the all-E content standard for biological lycopene extracted from *B. trispora*/natural source, by separating the all-E-C15-Wittig salts from the C15 phosphonium salts cis/trans mixture through a series of purification operations in aprotic solvents such as ethyl acetate, chloroform, acetone, methyl ethyl ketone, methyl isobutyl ketone, etc. The C15-Wittig salts so obtained include significantly high all-E content or high 6Z content. A C10-dialdehyde is then reacting with the high all-E containing or high 6Z containing C15 phosphonium salts in a double Wittig reaction, to obtain synthesized all-E-lycopenes or 5Z-lycopenes.

What is claimed is:

1. A method for purification of C15-Wittig salts to obtain high all-E contents, comprising the steps of:
    obtaining a C15-Wittig salt cis/trans mixture;
    purifying the C15-Wittig salt cis/trans mixture to remove solvents;
    adding an aprotic solvent to the C15 Wittig salt cis/trans mixture to extract 6Z-C15-Wittig salts from the mixture;
    removing the 6Z-C15-Wittig salts from the mixture to obtain residues; and
    purifying the obtained residues to obtain C15-Wittig salts;
    characterized in that the aprotic solvent comprises acetone.

2. The method according to claim 1, wherein purification of the C15 Wittig salt cis/trans mixture includes adding the aprotic solvent to the C15 Wittig salt cis/trans mixture and stirring the composition at 30° C. for over 10 hours.

3. The method according to claim 2, wherein the aprotic solvent includes ethyl acetate.

4. The method according to claim 2, wherein the composition is stirred for 16 hours.

5. The method according to claim 1, wherein purification of the residue includes adding the aprotic solvent to the C15 Wittig salt cis/trans mixture and stirring the composition at 25° C. to −30° C. for over 10 hours.

6. The method according to claim 5, wherein the aprotic solvent includes ethyl acetate.

7. A method for purification of C15-Wittig salts to obtain high 6Z contents, comprising the steps of:
    obtaining a C15-Wittig salt cis/trans mixture;
    purifying the C15-Wittig salt cis/trans mixture to remove solvents;
    adding an aprotic solvent to the C15 Wittig salt cis/trans mixture to extract 6Z-C15-Wittig salts from the mixture; and
    purifying the 6Z-C15-Wittig salts to obtain C15-Wittig salts;
    characterized in that the aprotic solvent comprises acetone.

8. The method according to claim 7, wherein purification of the C15 Wittig salt cis/trans mixture includes adding the aprotic solvent to the C15 Wittig salt cis/trans mixture and stirring the composition at 30° C. for over 10 hours.

9. The method according to claim 8, wherein the aprotic solvent includes ethyl acetate.

10. The method according to claim 7, wherein purification of the 6Z-C15-Wittig salts includes adding the aprotic solvent to the C15 Wittig salt cis/trans mixture and stirring the composition at 0° C. to 55° C., to obtain crystallized 6Z-C15-Wittig salts.

11. The method according to claim 10, wherein the composition is stirred at 40° C. to 50° C. for 2 hours.

12. The method according to claim 8, wherein the composition is stirred for 16 hours.

13. The method according to claim 7, wherein the extraction takes place at 40° C. to 50° C. of temperature for 2 hours.

14. The method according to claim 1, wherein the obtained C-15 Wittig salts are all E-isomer in 94.8% on the basis of HPLC analysis.

15. The method according to claim 5, wherein after filtration and drying, C15-Wittig salts with an E-isomer to Z-isomer ratio greater than 15:1 is obtained.

16. The method according to claim 10, wherein the ratio of the E isomer to the Z-isomer is from 1:33.5.

* * * * *